US00PP19115P2

(12) United States Plant Patent
Eskelund

(10) Patent No.: US PP19,115 P2
(45) Date of Patent: Aug. 19, 2008

(54) ROSE PLANT NAMED 'EVERA149'

(50) Latin Name: *Rosa hybrida*
Varietal Denomination: Evera149

(75) Inventor: Rosa Eskelund, Fåborg (DK)

(73) Assignee: Roses Forever ApS, Fåborg (DK)

( * ) Notice: Subject to any disclaimer, the term of this patent is extended or adjusted under 35 U.S.C. 154(b) by 0 days.

(21) Appl. No.: 11/784,549

(22) Filed: Apr. 6, 2007

(51) Int. Cl.
*A01H 5/00* (2006.01)

(52) U.S. Cl. ..... Plt./122

(58) Field of Classification Search ..... Plt./122, Plt./101
See application file for complete search history.

*Primary Examiner*—Annette H Para
(74) *Attorney, Agent, or Firm*—C. A. Whealy

(57) ABSTRACT

A new and distinct cultivar of Rose plant named 'Evera149', characterized by its upright and rounded plant habit; shiny dark green-colored leaflets; freely branching growth habit; freely flowering habit; large double red-colored flowers; flowers held upright on strong and erect peduncles; and good postproduction longevity.

1 Drawing Sheet

Botanical designation: *Rosa hybrida.*
Cultivar denomination: 'Evera149'.

BACKGROUND OF THE INVENTION

The present Invention relates to a new and distinct cultivar of Rose plant, botanically known as *Rosa hybrida,* commercially used as a potted Rose, and hereinafter referred to by the name 'Evera149'.

The new Rose is a product of a planned breeding program conducted by the Inventor in Fåborg, Denmark. The objective of the breeding program was to develop new uniform potted Rose varieties with novel and attractive flower colors, disease resistance and excellent postproduction longevity.

The new cultivar originated from a cross-pollination made by the Inventor on Feb. 1, 2004 of a proprietary Rose selection identified as code number 03-0322, not patented, as the female, or seed, parent with an unnamed Rose selection, not patented, as the male, or pollen, parent. The cultivar Ever149 was discovered and selected by the Inventor on Jan. 10, 2005 as a single flowering plant within the progeny of the stated cross-pollination in a controlled environment in Fåborg, Denmark.

Asexual reproduction of the new Rose by cuttings at Fåborg, Denmark since Nov. 1, 2005, has shown that the unique features of this new Rose are stable and reproduced true to type in successive generations of asexual reproduction.

SUMMARY OF THE INVENTION

The following traits have been repeatedly observed and are determined to be the unique characteristics of 'Evera149'. These characteristics in combination distinguish 'Evera149' as a new and distinct cultivar:

1. Upright and rounded plant habit.
2. Shiny dark green-colored leaflets.
3. Freely branching growth habit.
4. Freely flowering habit.
5. Large double red-colored flowers.
6. Flowers held upright on strong and erect peduncles.
7. Good postproduction longevity.

Plants of the new Rose differ from plants of the parent selections in the following characteristics:

1. Plants of the new Rose and the parent selections differ in plant habit.
2. Plants of the new Rose and the parent selections differ in flower color.

Plants of the new Rose can be compared to plants of the Rose cultivar Evera 121, disclosed in U.S. Plant Pat. No. 17,034. In side-by-side comparisons conducted in Fåborg, Denmark, plants of the new Rose differed from plants of the cultivar Evera 121 in the following characteristics:

1. Plants of the new Rose had longer internodes than plants of the cultivar Evera 121.
2. Plants of the new Rose had more thorns than plants of the cultivar Evera 121.
3. Plants of the new Rose had larger leaves than plants of the cultivar Evera 121.
4. Plants of the new Rose and the cultivar Evera 121 differed in leaf base shape.
5. Plants of the new Rose had larger flowers than plants of the cultivar Evera 121.
6. Plants of the new Rose and the cultivar Evera 121 differed in flower color as plants of the cultivar Evera 121 had pink-colored flowers.
7. Plants of the new Rose had more stamens and pistils per flower than plants of the cultivar Evera 121.

BRIEF DESCRIPTION OF THE PHOTOGRAPHS

The accompanying colored photographs illustrate the overall appearance of the new Rose, showing the colors as true as it is reasonably possible to obtain in colored reproductions of this type. Colors in the photographs may differ slightly from the color values cited in the detailed botanical description which accurately describe the colors of the new Rose.

The photograph at the top of the sheet comprises a side perspective view of a typical plant of 'Evera149' grown in a container.

The photograph at the bottom of the sheet is a close-up view of a typical flower of 'Evera149'.

DETAILED BOTANICAL DESCRIPTION

The new Rose has not been observed under all possible environmental conditions. The phenotype may vary somewhat with variations in environment such as temperature and light intensity, without, however, any variance in genotype. The aforementioned photographs, following observations and measurements describe plants grown during the autumn and winter in Fåborg, Denmark, in a glass-covered greenhouse and under commercial production practices. Plants were pinched one time and were about 12 to 14 weeks old when the photographs and description were taken. During the production of the plants, day temperatures averaged 22° C., night temperatures averaged 21° C. and light levels were about 20,000 lux. Three cuttings were grown in 15-cm containers. Plants used in the description represent a single plant. In the following description, color references are made to The Royal Horticultural Society Colour Chart, 2001 Edition, except where general terms of ordinary dictionary significance are used.

Botanical classification: *Rosa hybrida* cultivar Evera149.

Parentage:

*Female, or seed, parent.*—Proprietary seedling selection of *Rosa hybrida* identified as code number 03-0322, not patented.

*Male, or pollen, parent.*—Unnamed selection of *Rosa hybrida,* not patented.

Propagation:

*Type.*—By cuttings.

*Time to initiate roots.*—About ten to twelve days at 24° C.

*Time to produce a rooted young plant.*—About four weeks at 24° C.

*Root description.*—Fibrous, fleshy, medium thickness; white in color.

*Rooting habit.*—Freely branching; moderately dense.

Plant description:

*Plant form.*—Upright and rounded plant habit.

*Growth habit.*—Moderately vigorous. Freely branching habit; about three to four lateral branches develop from the pinch; dense and bushy growth habit.

*Plant height.*—About 25 cm to 35 cm.

*Plant width (spread).*—About 20 cm to 30 cm.

*Lateral branches.*—Length: About 23 cm to 33 cm. Diameter: About 3 mm. Internode length: About 2 cm to 3 cm. Strength: Moderately strong to strong. Texture: Smooth, glabrous. Color: Close to 147B. Thorns: Density: None to about eight per linear cm. Shape: Triangular with sharp acuminate apices. Height: About 4 mm to 6 mm. Diameter, at base: About 2 mm to 3.5 mm. Color, immature: Close to 151D. Color, mature: Close to 163D.

Foliage description:

*Arrangement.*—Alternate, compound with three to five leaflets per leaf.

*Leaf length.*—About 10.5 cm to 12.5 cm.

*Terminal leaflet length.*—About 5.5 cm to 7 cm.

*Lateral leaflet length.*—About 3 cm to 5 cm.

*Leaf width.*—About 8.5 cm to 9.5 cm.

*Terminal leaflet width.*—About 3.5 cm to 4 cm.

*Lateral leaflet width.*—About 2 cm to 3.3 cm.

*Leaflet shape.*—Ovate with cordate tendencies.

*Leaflet apex.*—Acuminate.

*Leaflet base.*—Cordate.

*Leaflet margin.*—Biserrate.

*Leaflet texture, upper and lower surfaces.*—Smooth, glabrous; leathery.

*Leaflet venation pattern.*—Pinnate; reticulate.

*Leaflet color.*—Developing leaflets, upper surface: Close to 137A. Developing leaflets, lower surface: Close to 147B. Fully developed, upper surface: Close to 147A; venation, close to 146A to 146B; shiny. Fully developed, lower surface: Close to 148B; venation, close to 147C.

*Petioles.*—Leaf petiole length: About 2.5 cm to 3 cm. Leaflet petiole length: About 2 mm to 3 mm Leaf petiole diameter: About 1.5 mm to 2 mm. Leaflet petiole diameter: About 1 mm. Leaf petiole texture, upper and lower surfaces: Glabrous; rough. Leaflet petiole texture, upper and lower surfaces: Smooth, glabrous. Leaf petiole color, upper surface: Darker than 199A. Leaf petiole color, lower surface: Close to 152A. Leaflet petiole color, upper surface: Close to 200C. Leaflet petiole color, lower surface: Close to 147C.

*Stipules.*—Quantity: Two per leaf. Length: About 0.8 cm to 1 cm. Width: About 1 mm. Shape: Lanceolate. Apex: Acuminate. Base: Truncate; sessile. Margin: Irregularly serrate. Texture, upper and lower surfaces: Smooth, glabrous; leathery. Color, upper surface: Close to 137C. Color, lower surface: Close to 137C.

Flower description:

*Flower type and habit.*—Large double red-colored flowers with numerous petals. Consistently symmetrical rosette flowers. Flowers borne singly on erect and strong peduncles; one terminal flower per lateral branch. Flowers persistent.

*Flowering season.*—Year-round under greenhouse conditions, optimal flowering from spring through autumn under garden conditions; flowering intermittent. Plants begin flowering about 78 days after planting.

*Flower diameter.*—About 7 cm to 9 cm.

*Flower depth (height).*—About 4 cm.

*Flower longevity on plant.*—About two weeks.

*Fragrance.*—Slightly fragrant; typical of *Rosa.*

*Flower buds (at stage of showering color).*—Shape: Ovoid. Length: About 2 cm. Diameter: About 1.8 cm. Color: Close to 138A.

*Petals.*—Quantity: Numerous; about 70 per flower arranged in numerous whorls. Length: About 4 cm to 5 cm. Width: About 5 cm to 5.5 cm. Shape: Close to orbicular. Apex: Rounded. Base: Attenuate. Margin: Entire. Texture, upper and lower surfaces: Smooth, glabrous; satiny. Color: When opening, upper surface: Brighter than 53B. When opening, lower surface: Close to 53C. Fully opened, upper surface: Brighter than 53B; with development, close to 53C. Fully opened, lower surface: Darker than 53D.

*Sepals.*—Quantity per flower: Typically five. Length: About 4 cm to 5 cm. Width: About 1 cm to 1.3 cm. Shape: Lanceolate. Apex: Sharply pointed. Base: Truncate. Texture, upper and lower surfaces: Pubescent; leathery. Color: When opening, upper surface: Close to 191A. When opening, lower surface: Close to 138A. Fully expanded, upper surface: Close to 138B. Fully expanded, lower surface: Close to 143A.

*Peduncles.*—Strength: Strong; flexible. Aspect: Mostly erect. Length: About 5 cm to 8 cm. Diameter: About 3 mm to 6 mm. Texture: Rough. Color: Close to 144A.

*Reproductive organs.*—Stamens: Quantity: About 75 per flower. Anther length: About 2 mm to 4 mm. Anther shape: Reniform. Anther color: Close to 7D. Filament color: Close to 53C. Pollen amount: None observed. Pistils: Quantity: About 125 per flower. Pistil length: About 4 mm. Stigma color: Close to 8D. Style length: About 3 mm to 5 mm. Style color: Close to 53B. Receptacle shape: Funnel-shaped. Receptacle height: About 8 mm. Receptacle diameter: About 1.3 cm. Receptacle texture: Smooth, glabrous. Receptacle color: Close to 144A. Seed/fruit: Seed and fruit production has not been observed.

Pathogen/pest resistance: Plants of the new Rose have not been observed to be resistant to pathogens and pests common to Roses.

It is claimed:

1. A new and distinct Rose plant named 'Evera149' as illustrated and described.

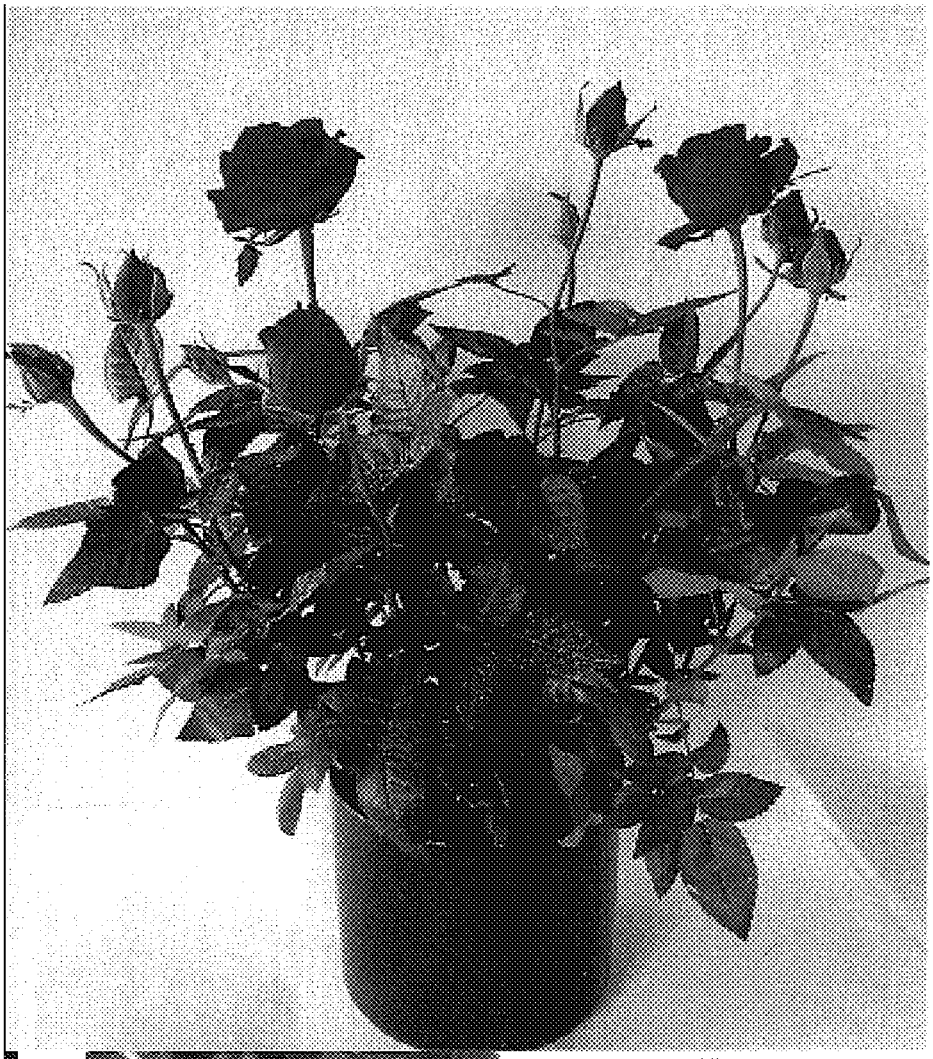
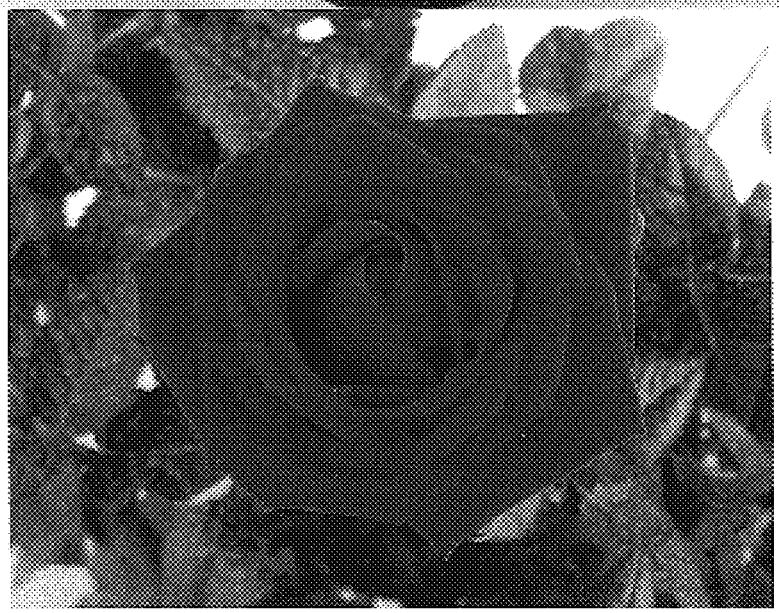

* * * * *